United States Patent
Synowicki et al.

(10) Patent No.: US 8,692,985 B1
(45) Date of Patent: Apr. 8, 2014

(54) METHOD OF DETERMINING REFRACTIVE INDEX OF PRISM SHAPED MATERIAL

(71) Applicants: Ronald A. Synowicki, Lincoln, NE (US); Greg K. Pribil, Lincoln, NE (US); Andrew C. Martin, Waverly, NE (US)

(72) Inventors: Ronald A. Synowicki, Lincoln, NE (US); Greg K. Pribil, Lincoln, NE (US); Andrew C. Martin, Waverly, NE (US)

(73) Assignee: J.A. Woollam Co., Inc., Lincoln, NE (US)

( * ) Notice: Subject to any disclaimer, the term of this patent is extended or adjusted under 35 U.S.C. 154(b) by 0 days.

(21) Appl. No.: 13/815,624

(22) Filed: Mar. 13, 2013

Related U.S. Application Data

(60) Provisional application No. 61/796,706, filed on Nov. 19, 2012, provisional application No. 61/848,760, filed on Jan. 11, 2013.

(51) Int. Cl.
*G01N 21/41* (2006.01)

(52) U.S. Cl.
CPC ............ *G01N 21/41* (2013.01); *G01N 21/4133* (2013.01)
USPC ............................ 356/128; 356/135; 356/137

(58) Field of Classification Search
CPC .................. G01N 21/41; G01N 21/4133
USPC .................................................. 356/128–137
See application file for complete search history.

(56) References Cited

U.S. PATENT DOCUMENTS

| | | | |
|---|---|---|---|
| 2,413,208 A | 12/1946 | Barner | |
| 2,649,013 A | 8/1953 | Schnelle | |
| 2,649,014 A | 8/1953 | Johnsen | |
| 2,972,926 A | 2/1961 | Goldberg et al. | |
| 2,090,222 A | 5/1963 | Ahaboshi | |
| 3,449,051 A | 6/1969 | Levitt | |
| 3,450,476 A | 6/1969 | Rando | |
| 3,797,940 A | 3/1974 | King | 356/134 |
| 4,284,352 A | 8/1981 | Carson et al. | 356/134 |
| 4,286,873 A | 9/1981 | Carson et al. | 356/130 |
| 4,381,895 A | 5/1983 | Hughes et al. | 356/134 |
| 4,756,618 A | 7/1988 | Spry | 356/134 |
| 5,125,740 A * | 6/1992 | Sato et al. | 356/128 |
| 5,696,580 A | 12/1997 | Kubo et al. | 356/72 |
| 6,549,276 B1 | 4/2003 | Longtin | 356/128 |
| 6,970,256 B1 * | 11/2005 | Jackson | 356/630 |
| 7,280,194 B1 | 10/2007 | Herzinger et al. | 356/128 |
| 7,456,942 B1 * | 11/2008 | Curley et al. | 356/136 |
| 2003/0156278 A1 * | 8/2003 | Yilmaz et al. | 356/135 |
| 2007/0058171 A1 * | 3/2007 | Berg et al. | 356/446 |
| 2011/0194109 A1 * | 8/2011 | Kahre | 356/326 |
| 2013/0182245 A1 * | 7/2013 | Yasunaga et al. | 356/135 |

\* cited by examiner

*Primary Examiner* — Sang Nguyen
(74) *Attorney, Agent, or Firm* — James D. Welch

(57) ABSTRACT

Methodology of determining refractive index and extinction coefficient of a prism shaped material, including simultaneously for a multiplicity of wavelengths using an easy to practice technique.

21 Claims, 6 Drawing Sheets

METHOD OF DETERMINING REFRACTIVE INDEX OF PRISM SHAPED MATERIAL

This Application Claims benefit of Provisional Applications Nos. 61/796,706 filed Nov. 19, 2012, and 61/848,760 Filed Jan. 11, 2013.

TECHNICAL FIELD

The present invention relates to methodology for determining refractive index and extinction coefficient values of a material, and more particularly to a method of quickly doing so for a multiplicity of wavelengths utilizing a (θ)-(θ) sample investigation system, for a material that is prism shaped and positioned in a system that uses electromagnetic radiation to investigate samples, having source and detector side arms that rotate about a common axis.

BACKGROUND

In 2007, Herzinger et al. Patented, (U.S. Pat. No. 7,280,194), Methodology for determining Refractive Indicies of solid and fluid materials by placing a prism shaped material on a stage in a (θ)-(2θ) goniometer system, that rotates about an axis. This geometry makes the method thereof difficult to practice in a typical dual arm ellipsometer or the like system, in which the arms secure a source and a detector respectively, and typically rotate about a horizontally oriented axis to enable projecting a beam of electromagnetic radiation at a sample on a centrally located stage. The present invention provides an approach for arriving at a similar result to that provided by Herzinger et al. 194, using an alternative sample investigation system arrangement.

In the context of the present invention, the method of determining the refractive index of a prism shaped material in U.S. Pat. No. 7,280,194, can be generally described as comprising the steps of:

a) providing a system comprising:
  a1) a stage for supporting said prism shaped material;
  a2) a fixed position source of a beam of electromagnetic radiation mounted on a source side of said stage for supporting said prism shaped material, and a detector of a beam of electromagnetic radiation mounted to a support arm on a detector side of said stage for supporting a prism shaped material; the positioning of said source of a beam of electromagnetic radiation defining an input angle of incidence to a source side of a prism shaped material when it is positioned on said stage, such that a beam of electromagnetic radiation from said source can be directed to enter the source side of said prism shaped material, be refracted thereby, pass through said prism shaped material and exit from said detector side of said prism shaped material at a refracted exit angle to said detector side of said prism shaped material, and then proceeds toward and enters said detector of beam of electromagnetic radiation;
  a3) a means for rotating the detector side support arm to which said detector is attached, and a means for rotating said stage for supporting said prism shaped material, each through a range of angles.

Said method then further comprises:

b) mounting a prism shaped material to said stage, said prism shaped material having converging input and detector sides that form an apex angle "A" where they intersect;

c) while causing said fixed position source of a beam of electromagnetic radiation to provide a beam of electromagnetic radiation directed toward the source side of said prism shaped material at a fixed angle of incidence to the source side thereof, rotating said stage for supporting said prism shaped material and rotating said support arm on said detector side of said prism shaped material to which said detector is attached to selected positions, and monitoring the intensity of the beam entering said detector as a result.

And finally, d) while monitoring intensity at the detector to enable determining the minimum deviation condition angle, identify the optimum rotation angles of said stage for supporting said prism shaped material and said support arm on said detector side of said prism shaped material to which said detector is attached, repeating step c) for multiplicity of rotations of said stage for supporting said prism shaped material and said support arm on said detector side of said prism shaped material to which said detector is attached until optimum angles of rotations for both the stage for supporting said prism shaped material and support arm on said detector side of said prism shaped material to which said detector is attached where the minimum deviation condition is achieved, (i.e. where the intensity is maximum), and identifying the rotation angles of the stage and support arm on said detector side of said prism shaped material to which said detector is attached as the optimum angle;

e) for the optimum angle determined in step d) applying the following formula:

$$n2 = \frac{(\sin((A + \delta\min)/2))}{\sin(A/2)} n1$$

to determine n2.

Note, n1 and n2 are the refractive indicies of the ambient environment surrounding said prism shaped material, and of said prism shaped material, respectively.

It is noted that this approach utilizes a sample monitoring system in which, for each degree (θ) a beam of electromagnetic radiation from the source is changed to provide, an angle of incidence to the sample, the detector angle is changed (2θ). That is, it utilizes a (θ)-(2θ) goniometer system. This involves the detector arm angle being moved as a slave to the source arm angle and then locked in place. The present invention, it will be presented later in this specification, provides for each of the source and detector arms to be moved equal amounts in a (θ)-(θ) system arrangement, rather than utilize a (θ)-(2θ) system arrangement.

Said method involves investigating a solid prism shaped material, or can have an empty volume in said prism shaped material into which is caused to be present a liquid, the optical constants of which are desired to be determined.

Said method can involves using a source of electromagnetic radiation which is spectroscopic and wherein said method is repeated a plurality of times, for a plurality of wavelengths, to determine refractive index at each thereof.

Said method typically involves application of (θ)-(2θ) means for adjusting each of the stage and detector sides support arm while holding the source side arm stationary. The mechanism that adjusts each of the stage and detector side support arm can enable manual or automatic simultaneous adjustment.

Even in view of the foregoing, need remains for an easy to practice method of determining refractive indicies of a prism shaped material, especially when a spectroscopic beam of electromagnetic radiation is used and refractive indicies are to be quickly determined for a multiplicity of wavelengths in a single sweep of source and detector angles-of-entry and exit from the prism shaped material.

DISCLOSURE OF THE INVENTION

Where one wavelength in a beam of electromagnetic radiation is to be investigated at a time, the present invention is a method of determining the refractive index of a prism shaped material, comprises the steps of:
  a) providing a system comprising:
   a1) a stage for supporting said prism shaped material,
   a2) a source of a beam of electromagnetic radiation:
    mounted directly on a rotatable support arm on a source side of said prism shaped material; or
    mounted other than on a rotatable support arm on a source side of said prism shaped material and also providing a beam directing beam director attached to said support arm on a source side of said prism shaped material; and
    providing a detector of a beam of electromagnetic radiation so that it is:
    mounted directly on a separate rotatable support arm on a detector side of said prism shaped material, or
    mounted other than on a rotatable support arm on a detector side of said prism shaped material and also providing a beam directing beam director attached to said rotatable support arm on a detector side of said prism shaped material.
  Each of source and detector side rotatable support arms are rotatable about a common axis so as to enable directing a beam of electromagnetic radiation provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward and enters said detector of beam of electromagnetic radiation.
  Said method also involves providing:
   a3) means for adjusting each of the source side and detector side rotatable support arms through equal angles by rotation about said common axis.
  The method then proceeds with the following steps:
   b) mounting a prism shaped material to said stage, said prism shaped material having converging input and detector sides that form an apex angle "A" where they intersect;
   c) while causing said source of a beam of electromagnetic radiation to provide a beam of electromagnetic radiation, rotating said rotatable support arm on said source side of said prism shaped material clockwise or counterclockwise some number of degrees to direct a beam of electromagnetic radiation toward the source side of said prism shaped material at an angle of incidence to said source side thereof, and rotating said separate rotatable support arm on said detector side of said prism shaped material counterclockwise or clockwise respectively, to the same magnitude number of degrees as was the rotatable support arm to which the source is attached and monitoring the intensity of the beam entering said detector as a result;
   d) repeating step c) for multiplicity of additional input beam angles of incidence and monitoring the intensity of the beam entering said detector as a result for each said angle to determine the optimum angle of incidence of said electromagnetic beam with respect to said source side of said prism shaped material at which the detector indicates a maximum intensity; and
   e) for the optimum maximum intensity angle of incidence determined in step d) applying the following formula:

$$n2 = \frac{(\sin((A + (180 - 2(\theta)\text{optimum angle}))/2))}{\sin(A/2)} n1$$

to determine n2.
  It is understood that n1 and n2 are the refractive indicies of the ambient environment surrounding said prism shaped material, and of said prism shaped material, respectively, where n2, and possibly to a lesser extent n1, demonstrate wavelength dependence.
  The source of electromagnetic radiation can be spectroscopic and said method can be repeated a plurality of times, for a plurality of wavelengths, to determine refractive index at each thereof.
  A present invention method can involve using a source of electromagnetic radiation which is spectroscopic, and said method can be repeated a plurality of times for a plurality of wavelengths, to determine refractive index at each thereof. As disclosed above, this can be done one wavelength at a time, but a preferred approach is to sweep the support arms through a range of angles and acquire data simultaneously for a multiplicity of wavelengths. In that case a method of simultaneously determining the refractive index of a prism shaped material for a multiplicity of wavelengths, can comprise the steps of:
  a) providing a system comprising:
   a1) a stage for supporting said prism shaped material,
   a2) a source of a spectroscopic beam of electromagnetic radiation:
    mounted directly to a rotatable support arm on a source side of said prism shaped material, or
    mounted other than to said rotatable support arm and provides a spectroscopic beam via a beam director attached to a support arm on a source side of said prism shaped material;
    and a wavelength disperser and multi-element detector of different wavelengths in a beam of electromagnetic radiation mounted:
    mounted directly to a separate rotatable support arm on a detector side of said prism shaped material, or
    mounted other than to said rotatable support arm and directs a spectroscopic beam via a beam director attached to a support arm on a detector side of said prism shaped material.
  Said source side and detector side rotatable support arms are each rotatable about a common axis so as to enable directing a beam of electromagnetic radiation, provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward said wavelength disperser where it is dispersed into separate wavelengths which enter said detector of spectroscopic beam of electromagnetic radiation.
  Said method further comprises providing:
   a3) means for adjusting each of the source side and detector sides rotatable support arms through equal angles by rotation about said common axis.

The method then proceeds with the steps:

b) mounting a prism shaped material to said stage, said prism shaped material having converging input and detector sides that form an apex angle "A" where they intersect;

c) while causing said source of a beam of electromagnetic radiation to produce a spectroscopic beam of electromagnetic radiation, rotating said rotatable support arm on said source side of said prism shaped material counterclockwise or clockwise through a range of angles to direct a beam of electromagnetic radiation toward the source side of said prism shaped material at an angle of incidence to said source side thereof, and simultaneously, rotating said separate rotatable support arm on said detector side of said prism shaped material clockwise or counterclockwise, respectively, through the same range of angles as was the rotatable support arm to which the source is attached, and simultaneously monitoring the intensity of a multiplicity of dispersed wavelengths in said beam entering different detecting elements of said detector as a result;

d) monitoring the intensity of each of said multiplicity of dispersed wavelengths in the beam entering the multiple elements of said detector as a result by so doing determining the optimum angle of incidence of each wavelength in said electromagnetic beam with respect to said source side of said prism shaped material at which the detector indicates a maximum intensity; and e) for the optimum maximum intensity angle of incidence determined in step d) applying the following formula:

$$n2 = \frac{(\sin((A + (180 - 2(\theta)\text{optimum angle}))/2))}{\sin(A/2)} n1$$

to determine n2.

It is noted that n1 and n2 are the refractive indicies of the ambient environment surrounding said prism shaped material, and of said prism shaped material, respectively, where n2, and possible to a lesser extent n1, demonstrate wavelength dependence.

In either of the two methods disclosed above, it is noted that the stage for supporting said prism shaped material need not be rotatable, as is required in (θ)-(2θ) system described in that Background Section of this Specification, but it is able to be moved, for instance, up and down where the stage is mounted horizontally, in laboratory coordinates. In fact, the stage can be fixed in place as regards rotation in the present invention.

Also in either of the two methods disclosed above, said means for adjusting each of the source side and detector side rotatable support arms through equal angles, can involve providing a mechanism that adjusts each of the input and detector side rotatable support arms independently, or involves providing a theta (θ)-theta (θ) mechanism wherein adjusting the source side rotatable support arm automatically results in said detector side rotatable support arm being adjusted.

Further, in either method the prism shaped material can have an empty volume therein and into which is caused to be present a liquid, the optical constants of which are to be determined.

Also, in either of the two methods, where a prism shaped material is of a known refractive index its measured value can be used to calibrate the system so that it reads accurately, as well as repeatably. This would involve adjusting measurement system parameters so that the measured reading is what is expected for said known sample.

In either of the two methods the source of a spectroscopic beam of electromagnetic radiation can be directly attached to the said rotatable support arm on said source side of said prism shaped material, or a beam director can be attached thereto with the source located elsewhere, and likewise the beam diffractor and detector of electromagnetic radiation exiting said prism shaped material can be directly attached to said rotatable support arm on said detector side of said prism shaped material, or a beam director can be attached thereto and the actual detector of electromagnetic radiation be otherwise located.

Further either of the two methods can involve all method steps being carried out under control of a computer and/or can include storing at least some output provided by the detector in non-transitory machine readable media, and analyzing at least some output provided by the detector.

The step of providing said means for adjusting each of the source side and detector sides support arms through equal angles, can involve providing a mechanism that adjusts each of the input and detector side rotatable support arms independently, or can involve providing a theta (θ)-theta (θ) mechanism wherein adjusting the source side rotatable support arm, automatically results in said detector side rotatable support arm being adjusted.

The common axis about which the rotatable source side support and detector side support arms rotate can be oriented vertically or horizontally in lab coordinates.

Continuing, for either approach, the methodology can further comprise determining the extinction coefficient of said prism shaped material, by:

f) changing the position of said stage so that the electromagnetic beam passing therethrough passes through a different length of said prism shaped material, and monitoring the output of said detector of a beam of electromagnetic radiation to provide the intensity exiting said prism shaped material; and g) applying said intensity value obtained in step f, and the intensity value previously obtained in step c, and relating them to path lengths of said beam as it passes through said prism shaped material, to determine the extinction coefficient.

Note: Practice of steps f) and g) will typically involve changing of position of the stage by moving it, for instance, up or down where the stage is oriented horizontally. This will cause the beam to transverse different lengths, (e.g. (t1) and (t2) for the different positions of prism shaped material), as it passes therethrough, and this results in two different Intensities, (e.g. (I1) and (I2)), being monitored by the detector. Having said lengths and Intensities, the Extinction Coefficient can then be calculated from:

$$k(\lambda) = \frac{(\lambda \ln(I1/I2))}{4\pi(t2 - t1)}$$

The invention will be better understood by reference to the Detailed Description Section of this Specification, and the accompanying Drawings.

DETAILED DESCRIPTION

Figure 1:
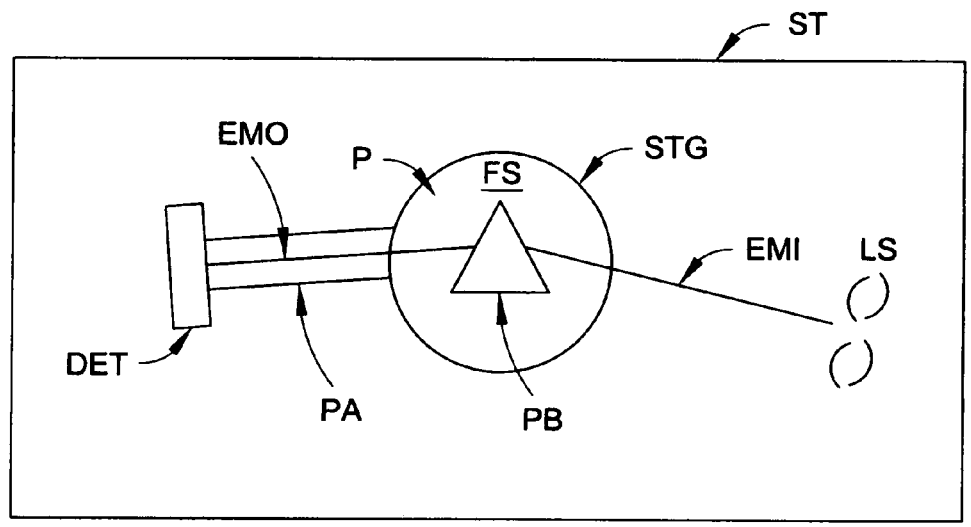
FIGS. 1 and 2 duplicate FIGS. 1 and 2 in the Herzinger U.S. Pat. No. 7,280,194.
Figure 2:
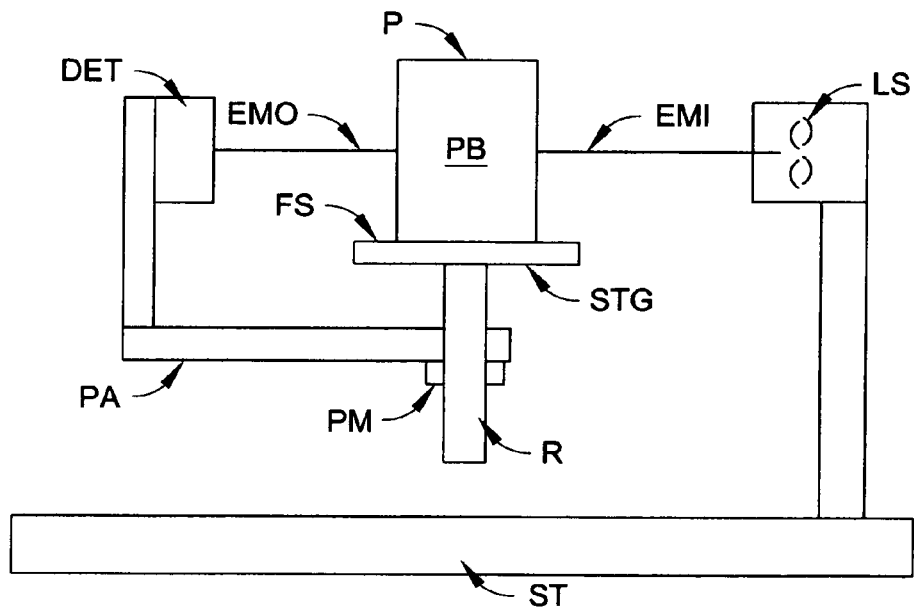

Turning now to the Drawings, FIGS. 1 and 2 duplicate FIGS. 1 and 2 in the Herzinger 194 Patent. The Stage (STG) is oriented so that its sample supporting Front Surface (FS) faces upward, and so that it can be rotated about a vertical axis, and the stationary Source (LS) of electromagnetic radiation, and rotatable Detector (DET) thereof move in a demonstrative horizontally oriented plane. Also shown are the Prism Bottom (PB), input (EMI) and output (EMO) beams of electromagnetic radiation, and Detector Support Arm (PA). This works well, but is inconsistent with many typical ellipsometer and other systems that comprise a Theta (θ)-Theta (θ) goniometer.

FIG. 2 also shows a Pivot Means (PM) and Rotor (R) used to rotate the Prism (PRI).

Figure 3:
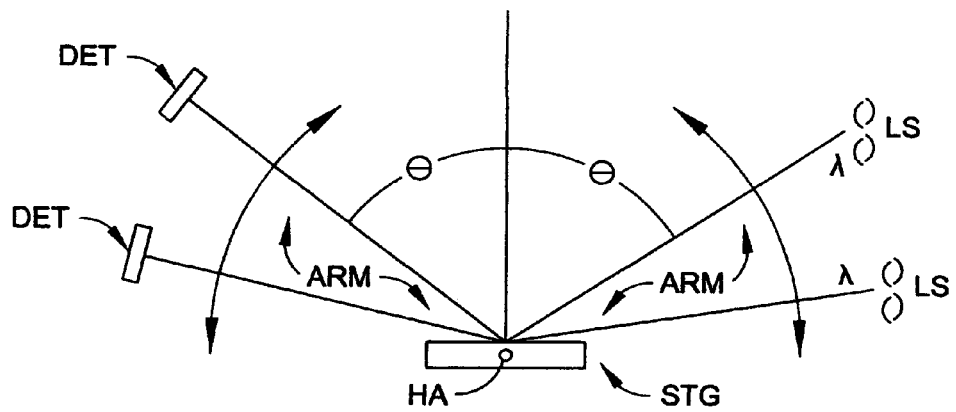
FIG. 3 shows a typical sample investigation system configuration with source and detector rotatable arms mounted in a (θ)-(θ) configuration.

FIG. 3 shows an alternative goniometer system configuration in an ellipsometer or other sample investigation system that utilizes electromagnetic beams. Note that a sample supporting Stage (STG) is shown facing upward for demonstrative purposes, and also that the Source (LS) of electromagnetic radiation (λ) and Detector (DET) thereof move in a vertically oriented plane in what can be termed a rotational motion that controls the angles (θ) of incidence of the electromagnetic radiation input beam (EMI) from said Source (LS) onto said Stage (STG) and its reflected angle toward the Detector (DET). Said Source (LS) and Detector (DET) are shown mounted to Arms (ARM) to enable said motion. It is noted that as shown, the stage (STG) can be provided the capability of moving up and down, and such capability is applied in the present invention to enable determination of prism material extinction coefficient. Further, it is to be understood that the system could be arranged to allow stage (STG) rotations about a demonstrative horizontal axis, rather than a vertically oriented axis. This capability is generally not utilized in the present invention methodology where the stage usually rotationally fixed, and rather is used only to align the Prism (PRI) to the optical system. The FIG. 3 configuration is consistent with many conventional ellipsometer, and other systems that utilize electromagnetic beams to investigate samples, such as those manufactured by the J.A. Woollam CO. In the practice of the present invention methodology the Stage (STG) is fixed in position and the Arms (ARM) are rotated in a demonstrative vertically oriented plane about a demonstrative horizontally oriented axis. (Note, in a (θ)-(2θ) configuration the Source (LS) can be fixed in position and the Arm (ARM) to which the Detector (DET) is attached, and the Stage (STG) can be rotated about demonstrative horizontally oriented axes). FIG. 3, however, is included to demonstrate a (θ)-(θ) goniometer scenario, with a rotation of the stage about a pivot (HA) used in the present invention methodology only to align the stage. That is, it is not rotated during data acquisition as is the case where a (θ)-(2θ) system as in FIGS. 1, 2, 5 and 6 is utilized.

Figure 4:
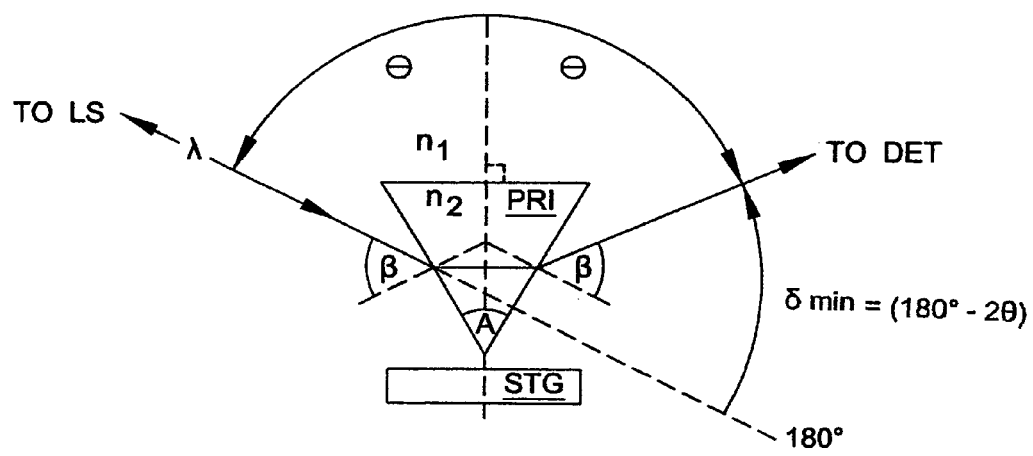
FIG. 4 shows that where a Prism Shaped Material (PRI) is placed on a stage (STG) the (θ)-(θ) goniometer scenario is altered in that the Theta (θ) angles of incidence and exit are changed by said Prism Shaped Material (PRI).

FIG. 4 shows where a Prism Shaped Material (PRI) is placed on a stage (STG) a (θ)-(θ) goniometer scenario, (such as demonstrated in FIG. 3), that the path of the electromagnetic beam (λ) is altered when it enters the Prism (PRI) such that the angles of incidence and exit are changed by refraction. Note that a "Deviation Angle" (δ=180−(2θ)) is identified. And, where the angles (β) are made to be equal by rotation of the Source (LS) and Detector (DET) locations in a vertically oriented plane, what is termed the "Minimum Deviation" (δ min=180−(2θ)) condition can be achieved. At that condition the Refractive Index (n2) can be calculated.

Figure 5:
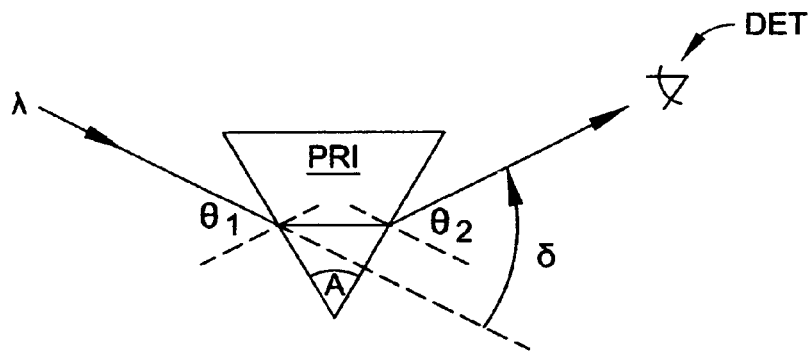
FIGS. 5 & 6 indicates a traditional (θ)-(2θ) goniometer configuration that can be applied to determine the refractive index utilizing a Stage (STG) and a Detector (DET) that can each be rotated. Note that (A) is an angle measured in degrees just as is (θ).
Figure 6:
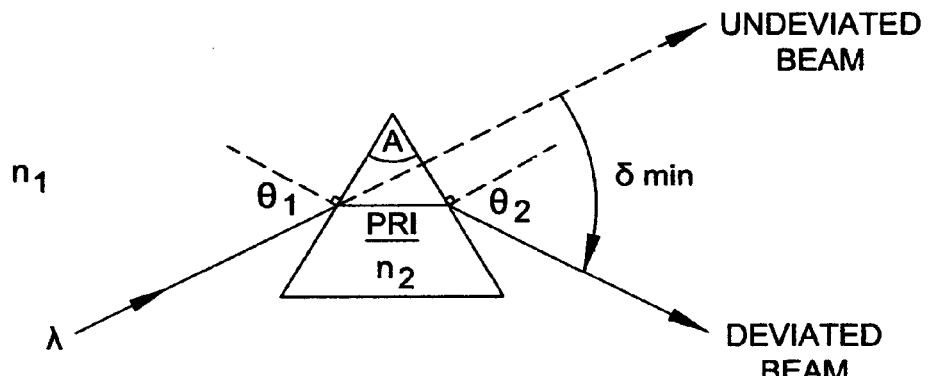

FIGS. 5 and 6 indicate a traditional (θ)-(2θ) approach to achieving a similar result wherein the Stage (STG) and Detector (DET) are rotated in a Vertically oriented plane. FIGS. 1, 2, 5 and 6 are included to provide contrast to the (θ)-(θ) system utilized in the present invention methodology, insight to which is provided in FIGS. 3, 4 and 7. Shown in FIGS. 5 and 6 are an input beam of electromagnetic radiation (λ), a dashed line that indicates an undeviated input beam, angles (θ1) and (θ2) that form between perpendiculars to the input and output sides of the Prism (PRI) and the input (λ) and Deviated output beams, and an indication that a condition of (δ min) exists when (θ1)=(θ2), and the beam locus in the Prism (PRI) is parallel to the third side thereof. Also shown are refractive indicies (n1) and (n2). Note that the Prism (PRI) can be oriented so that its Apex Angle "A" projects upward or downward.

Figure 7:
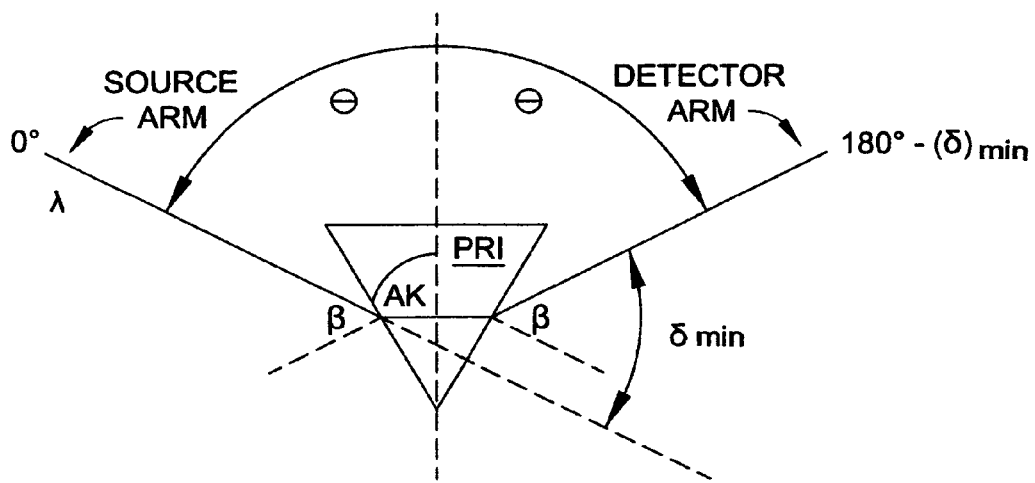
FIG. 7 shows a goniometer system for practicing the present invention Minimum Deviation (θ)-(θ) method that enables an intensity measurement approach to determining the Refractive Index of a Prism Shaped Material (PRI).

FIG. 7 shows a Prism Shaped Material mounted in a FIG. 3 type (θ)-(θ) system which it is applied in a present invention method of determining the Refractive Index thereof. Shown are Source and Detector Arms, which can support a source of, and detector of a beam of electromagnetic radiation respectively, or means for attaching a beam director thereto. Importantly, where the angles (β) on the source and output sides of the Prism (PRI) are equal and the beam locus in the Prism (PRI) is parallel to the third side of the Prism (PRI), (i.e. that side not serving as beam intercepting input and output sides thereof), than the (δ) angle, which is the angle between the dashed line that represents an undeviated beam, and a beam locus identified as (180−(δ)) will satisfy a minimum deviation condition. Knowing that allows calculating the refractive index of the Prism material, given that of the ambient.

Figure 8A:
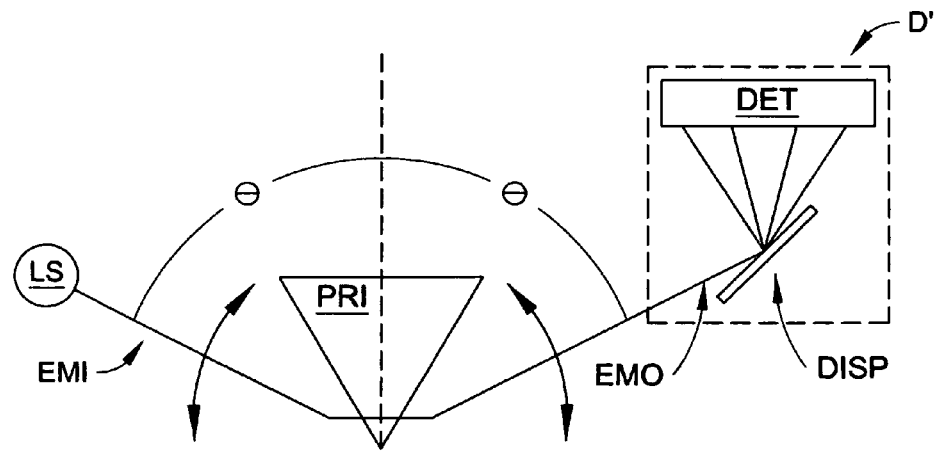
FIGS. 8a and 8b show a system for practicing a very beneficial simultaneous multiple wavelength method of the present invention.
Figure 8B:
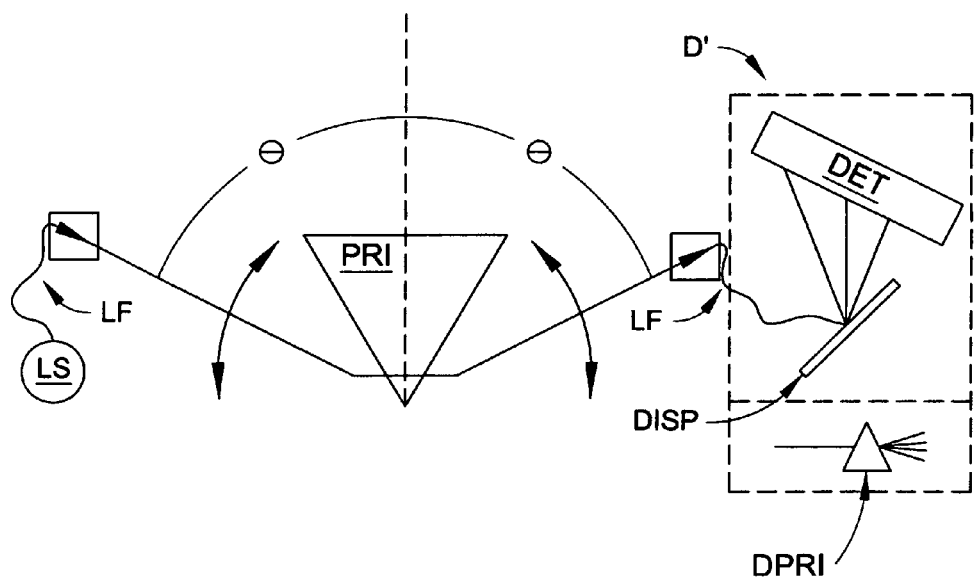
Figure 9:
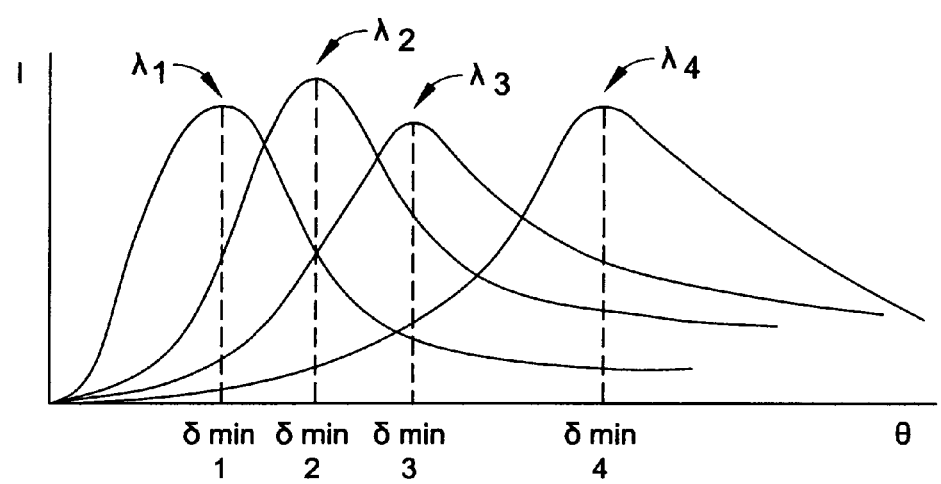
FIG. 9 plot is developed either actually or in a computer memory for multiple wavelengths.

FIGS. 8a and 8b show a source (LS) of a spectroscopic beam of electromagnetic radiation, a Prism shaped material, a Disperser (DISP) and a Detector (DET) that form a unit (D'). In use (LS) and (D'), and therefore the beams (EMI) and (EMO) are scanned through equal Theta (A) angles, but one clockwise and the other counterclockwise, while a FIG. 9 plot is developed either actually or in a computer memory. Note that for each wavelength monitored a different minimum deviation peak intensity is identified for each wavelength (λ1), (λ2), (λ3) and (λ4), which correspond to different minimum deviation angles of (δ1), (δ2), (δ3) and (δ4). That is, in one scan through of (EMI) and (EMO) through a range of Theta (θ) angles can provide Refractive Indicies for a multiplicity of wavelengths. This is much faster than is typically possible in traditional known approaches and, again, utilizes a (θ)-(θ) goniometer system. The speed of data acquisition is a very important aspect enabled by of the present invention methodology. Also indicated in FIG. 8b is that a wavelength dispersing element can be a grating (DISP) or prism (DPRI). However, any wavelength dispersing element can be used that directs different wavelengths into different detector elements.

It is noted that FIGS. 8a and 8b should be interpreted to allow a beam directing beam director, (e.g. an optical fiber (LF)), to be attached at only one of the source and detector sides, or on both source and detector sides, or on neither side as demonstrated in FIG. 3 where the Source (LS) and Detector (DET) are directly mounted to the Supports (ARM).

Figure 10:
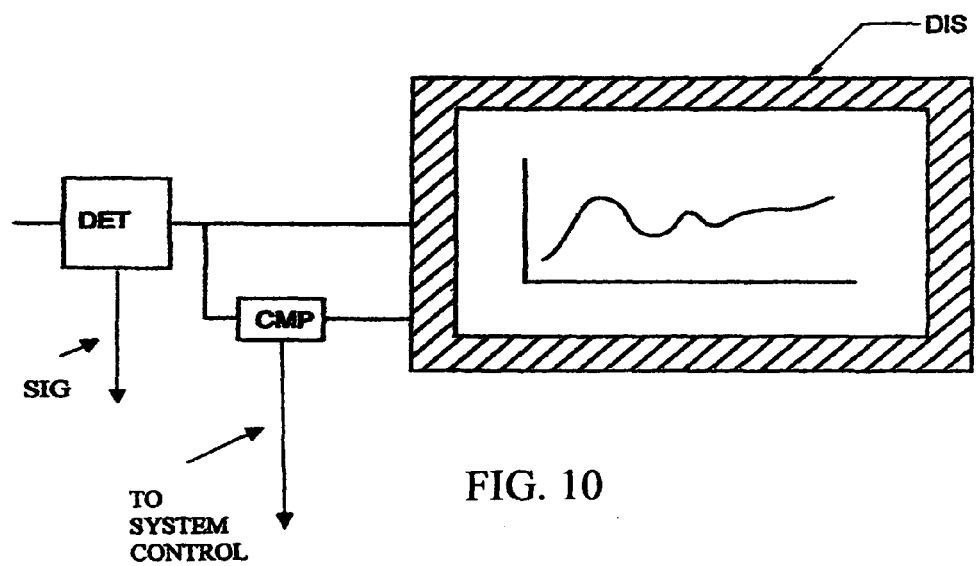
FIG. 10 is included to show that the method steps of the present invention system can be controlled by a computer (CMP).

FIG. 10 is included to show that the method steps of the present invention system can be controlled by a computer (CMP). Note, a Signal (SIG) from the Detector (DET) can be also be directed to said computer (CMP), or another computer to analyze data and provide an output plot as in FIG. 9.

Finally, it is noted that generally herein (δ min) refers to an "optimum angle" (θ), whereat intensity from the Detector peaks for a given wavelength.

Having hereby disclosed the subject matter of the present invention, it should be obvious that many modifications, substitutions, and variations of the present invention are possible in view of the teachings. It is therefore to be understood that the invention may be practiced other than as specifically described, and should be limited in its breadth and scope only by the Claims.

We claim:

1. A method of determining the refractive index of a prism shaped material, comprising the steps of:

a) providing a system comprising:

a1) a stage for supporting said prism shaped material, a2) a source of a beam of electromagnetic radiation:

mounted directly on a rotatable support arm on a source side of said prism shaped material; or mounted other than on a rotatable support arm on a source side of said prism shaped material and also providing a beam directing beam director attached to said support arm on a source side of said prism shaped material;

and positioning a detector of a beam of electromagnetic radiation:

mounted directly on a separate rotatable support arm on a detector side of said prism shaped material, or mounted other than on a rotatable support arm on a detector side of said prism shaped material and also providing a beam directing beam director attached to said rotatable support arm on a detector side of said prism shaped material;

each of said sample and detector side rotatable supports being rotatable about a common axis so as to enable directing a beam of electromagnetic radiation provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward and enters said detector of beam of electromagnetic radiation;

a3) means for adjusting each of the source side and detector sides rotatable support arms through equal angles by rotation about said common axis; and a4) a computer;

b) mounting a prism shaped material to said stage, said prism shaped material having converging input and detector sides that form an apex angle "A" where they intersect;

c) while causing said source of a beam of electromagnetic radiation to provide a beam of electromagnetic radiation, rotating said rotatable support arm on said source side of said prism shaped material clockwise or counterclockwise some number of degrees to direct a beam of electromagnetic radiation toward the source side of said prism shaped material at an angle of incidence to said source side thereof, and rotating said separate rotatable support arm on said detector side of said prism shaped material counterclockwise or clockwise respectively, to the same magnitude number of degrees as was the rotatable support arm to which the source is attached and monitoring the intensity of the beam entering said detector as a result;

d) repeating step c) for multiplicity of additional input beam angles of incidence and monitoring the intensity of the beam entering said detector as a result for each said angle to determine the optimum angle of incidence of said electromagnetic beam with respect to said source side of said prism shaped material at which the detector indicates a maximum intensity; and e) for the optimum maximum intensity angle of incidence determined in step d), in said computer, applying the following formula:

$$n2 = \frac{\sin((A + (180 - 2(\theta)\text{optimum angle}))/2))}{\sin(A/2)} n1$$

to determine n2,
where n1 and n2 are the refractive indicies of the ambient environment surrounding said prism shaped material, and of said prism shaped material, respectively.

2. A method as in claim 1, wherein the source of a spectroscopic beam of electromagnetic radiation is directly attached to the said rotatable support arm on said source side of said prism shaped material, and wherein the beam diffractor and detector of electromagnetic radiation exiting said prism shaped material is directly attached to said rotatable support arm on said detector side of said prism shaped material.

3. A method as in claim 1, wherein the source of a spectroscopic beam of electromagnetic radiation provides a beam that is directed to the prism shaped material by a beam director that is attached to the said support arm on said source side of said prism shaped material, and/or wherein the beam of electromagnetic radiation exiting said prism shaped material is directed to the beam diffractor and detector by a beam director that is attached to said support arm on said detector side of said prism shaped material.

4. A method as in claim 1, wherein the step of providing said means for adjusting each of the source side and detector sides rotatable support arms through equal angles, involves providing a mechanism that adjusts each of the input and detector side rotatable support arms independently.

5. A method as in claim 1, wherein the step of providing said means for adjusting each of the source side and detector sides rotatable support arms through equal angles, involves providing a theta (θ)-theta (θ) mechanism wherein adjusting the source side rotatable support arm, automatically results in said detector side rotatable support arm being adjusted.

6. A method as in claim 1, in which the prism shaped material has an empty volume therein and into which is caused to be present a liquid, the optical constants of which are to be determined.

7. A method as in claim 1, in which the source of electromagnetic radiation is spectroscopic and wherein said method is repeated a plurality of times, for a plurality of wavelengths, to determine refractive index at each thereof.

8. A method as in claim 1, which further comprises determining the extinction coefficient of said prism shaped material, by:
  f) changing the position of said stage so that the electromagnetic beam passing therethrough passes through a different length of said prism shaped material, and monitoring the output of said detector of a beam of electromagnetic radiation to provide the intensity exiting said prism shaped material; and
  g) applying said intensity value obtained in step f, and the intensity value previously obtained in step c, and relating them to path lengths of said beam as it passes through said prism shaped material, to determine the extinction coefficient.

9. A method as in claim 1, in which the common axis about which the rotatable source side support and detector side support arms rotate is oriented substantially horizontally, or substantially vertically in lab coordinates.

10. A method as in claim 1 wherein the prism shaped material is of a known refractive index, and wherein its measured value is used to calibrate the system so that it reads accurately as well as repeatably.

11. A method as in claim 1, in which all method steps are carried out under control of a computer and/or the method includes storing at least some output provided by the detector in non-transitory machine readable media, and analyzing at least some output provided by the detector.

12. A method of simultaneously determining the refractive index of a prism shaped material for a multiplicity of wavelengths, comprising the steps of:
  a) providing a system comprising:
    a1) a stage for supporting said prism shaped material,
    a2) a source of a spectroscopic beam of electromagnetic radiation:
      mounted directly to a rotatable support arm on a source side of said prism shaped material, or
      mounted other than to said rotatable support arm and provides a spectroscopic beam via a beam director attached to a support arm on a source side of said prism shaped material;
    and a wavelength disperser and multi-element detector of different wavelengths in a beam of electromagnetic radiation mounted:
      mounted directly to a separate rotatable support arm on a detector side of said prism shaped material, or
      mounted other than to said rotatable support arm and directs a spectroscopic beam via a beam director mounted to a support arm on a detector side of said prism shaped material;
      said source side and detector side rotatable support arms each being rotatable about a common axis so as to enable directing a beam of electromagnetic radiation, provided by said source of a beam of electromagnetic radiation, at various angles of incidence to said source side of said prism shaped material such that it enters said prism shaped material, is refracted thereby, passes through said prism shaped material and exits from said detector side of said prism shaped material at a refracted exit angle to said detector side of said prism shaped material, and then proceeds toward said wavelength disperser where it is dispersed into separate wavelengths which enter said detector of spectroscopic beam of electromagnetic radiation;
    a3) means for adjusting each of the source side and detector sides rotatable support arms through equal angles by rotation about said common axis; and
    a4) a computer;
  b) mounting a prism shaped material to said stage, said prism shaped material having converging source and detector sides that form an apex angle "A" where they intersect;
  c) while causing said source of a beam of electromagnetic radiation to produce a spectroscopic beam of electromagnetic radiation, rotating said rotatable support arm on said source side of said prism shaped material counterclockwise or clockwise through a range of angles to direct a beam of electromagnetic radiation toward the source side of said prism shaped material at an angle of incidence to said source side thereof, and rotating said separate rotatable support arm on said detector side of said prism shaped material clockwise or counterclockwise, respectively, through the same range of angles as was the rotatable support arm to which the source is attached, and simultaneously monitoring the intensity of a multiplicity of dispersed wavelengths in said beam entering different detecting elements of said detector as a result;
  d) monitoring the intensity of each of said multiplicity of dispersed wavelengths in the beam entering the multiple elements of said detector as a result by so doing determining the optimum angle of incidence of each wavelength in said electromagnetic beam with respect to said source side of said prism shaped material at which the detector indicates a maximum intensity; and
  e) for the optimum maximum intensity angle of incidence determined in step d), in said computer, applying the following formula:

$$n2 = \frac{(\sin((A + (180 - 2(\theta)\text{optimum angle}))/2))}{\sin(A/2)} n1$$

to determine n2,
where n1 and n2 are the refractive indicies of the ambient environment surrounding said prism shaped material, and of said prism shaped material, respectively;
where n2 is wavelength dependent.

13. A method as in claim 12, wherein the source of a spectroscopic beam of electromagnetic radiation is directly attached to the said rotatable support arm on said source side of said prism shaped material, and wherein the beam diffractor and detector of electromagnetic radiation exiting said prism shaped material is directly attached to said rotatable support arm on said detector side of said prism shaped material.

14. A method as in claim 12, wherein the source of a spectroscopic beam of electromagnetic radiation provides a beam that is directed to the prism shaped material by a beam director that is attached to the said support arm on said source side of said prism shaped material, and/or wherein the beam of electromagnetic radiation exiting said prism shaped material is directed to the beam diffractor and detector by a beam director that is attached to said support arm on said detector side of said prism shaped material.

15. A method as in claim 12, wherein the step of providing said means for adjusting each of the source side and detector sides support arms through equal angles, involves providing a mechanism that adjusts each of the input and detector side rotatable support arms independently.

16. A method as in claim 12, wherein the step of providing said means for adjusting each of the source side and detector sides rotatable support arms through equal angles, involves providing a theta ($\theta$)-theta ($\theta$) mechanism wherein adjusting the source side rotatable support arm, automatically results in said detector side rotatable support arm being adjusted.

17. A method as in claim 12, in which the prism shaped material has an empty volume therein and into which is caused to be present a liquid, the optical constants of which are to be determined.

18. A method as in claim 12, which further comprises determining the extinction coefficient of said prism shaped material, by:

f) changing the position of said stage so that the electromagnetic beam passing therethrough passes through a different length of said prism shaped material, and monitoring the output of said detector of a beam of electromagnetic radiation to provide the intensity exiting said prism shaped material; and g) applying said intensity value obtained in step f, and the intensity value previously obtained in step c, and relating them to path lengths of said beam as it passes through said prism shaped material, to determine the extinction coefficient.

19. A method as in claim 12, in which the common axis about which the rotatable source side support and detector side support arms rotate is oriented substantially horizontally, or substantially vertically in lab coordinates.

20. A method as in claim 12 wherein the prism shaped material is of a known refractive index, and wherein its measured value is used to calibrate the system so that it reads accurately as well as repeatable.

21. A method as in claim 12, in which all method steps are carried out under control of a computer and/or the method includes storing at least some output provided by the detector in non-transitory machine readable media, and analyzing at least some output provided by the detector.

* * * * *